United States Patent [19]

Bruch et al.

[11] Patent Number: 5,403,864
[45] Date of Patent: Apr. 4, 1995

[54] RAPIDLY-ACTING TOPICAL ANTIMICROBIAL COMPOSITION

[75] Inventors: Mary Ruth K. Bruch, Hamilton; Donna B. Suchmann, Annandale, both of Va.

[73] Assignee: John A. Manfuso, Jr., Chevy Chase, Md.

[21] Appl. No.: 41,659

[22] Filed: Apr. 1, 1993

[51] Int. Cl.$^6$ .................... A01N 31/14; A01N 31/08
[52] U.S. Cl. .................... 514/721; 514/724; 514/737
[58] Field of Search ............... 424/670; 514/721, 724, 514/737

[56] References Cited

U.S. PATENT DOCUMENTS 2,350,677  6/1944  Gladden .
3,629,477 12/1971  Model .

OTHER PUBLICATIONS

Merck Index 10th ed pp. 34, 35.

Primary Examiner—Alan Siegel
Attorney, Agent, or Firm—Banner, Birch, McKie & Beckett

[57] ABSTRACT

A rapidly-acting topically applied antimicrobial composition is disclosed which comprises triclosan, chloroxylenol, and an alcohol or alcohol mixture.

7 Claims, No Drawings

RAPIDLY-ACTING TOPICAL ANTIMICROBIAL COMPOSITION

The present invention comprises a rapidly-acting antimicrobial composition which is topically applied.

BACKGROUND OF THE INVENTION

Infection control and epidemiology experts have repeatedly emphasized that the single most important element in reducing the spread of infection is handwashing because a common method of transfer among individuals in the health care environment is with the hands. This fact has been painfully demonstrated in the analysis of epidemic spread.

However obvious and simple this may seem, medical care personnel, including physicians and nurses, are reluctant to wash or scrub their hands as frequently as required by their own protocols. It is estimated that the average time of washing between patients is 10 sec or less. The effectiveness of soap-and-water washing is measured in terms of minutes. Most simply do not wash frequently enough.

The product described herein is designed for repeated use by health care personnel when moving from patient to patient or procedure. The use of alcohol as an antimicrobial dates to biblical times and earlier. Its use was in vogue as a hand dip in the United States in the early years of this century, but it rapidly declined when new liquid soaps containing antimicrobials were introduced. A common complaint after the use of an alcohol dip was drying and chapping of the hands.

In Germany, Austria and Holland, alcohol has been widely accepted as an effective and useful hand rub and dip to the exclusion of most other types. The addition of emollients has eliminated some complaints relating to the natural action of alcohol as a defatting agent. Ethyl alcohol however does not defat in the same way that isopropyl alcohol act as a defatting agent.

Rotter in Austria has shown that a little-used alcohol, n-propyl or n-propanol is very effective, in fact, the most effective alcohol in reducing acquired microbial flora on the hands. When a health care worker handles equipment or patients, bacteria which are not a part of the normal skin flora are picked up and adhere loosely to the topmost skin layer, the stratum corneum.

It is the acquired and potentially pathogenic organisms that must be removed prior to handling another patient or medical device or before donning gloves. In recent years, serious outbreaks of infection and contamination in food and dairy plants have focused attention on handwashing by handlers of food and dairy products. Food, meat or dairy products provide a ready nutrient source for potentially pathogenic microorganisms acquired from natural sources or the handlers themselves.

SUMMARY OF THE INVENTION

It is the object of the present invention to provide an antimicrobial composition that is effective against a broad range of microorganisms, including pathogenic microorganisms that resist conventional antimicrobial compositions, that is easily applied as a topical composition, and that acts within seconds rather than minutes. Surprisingly, the present inventors have achieved this object with a composition comprising triclosan, chloroxylenol, and an alcohol or alcohol mixture.

DETAILED DESCRIPTION

More particularly, the present invention is a composition comprising from about 0.5 to about 3.0% by weight of triclosan, from about 0.5 to about 2.0% by weight of chloroxylenol, and from about 40 to about 70% by weight of an alcohol or alcohol mixture.

Alcohols—A variety of alcohols have been used in a multitude of concentrations. Isopropanol, although often used on the skin, is less desirable for use in the present invention because of its severe defatting tendency. Its defatting tendency may, however, be compensated for by adding sufficient emollient ingredient (as described herein). Preferred alcohols according to the present invention are ethyl and n-propyl. Ethyl alcohol has been the classic for medical application, but varies in effectiveness depending on the concentration and is regarded as the least effective relative to isopropyl and n-propyl. Normal propyl alcohol (n-propanol) has gained popularity in Austria and Germany because of its demonstrated effectiveness and from its use as a standard against which all other formulations are measured.

In the present invention, when more than one alcohol is used, the alcohols are mixed at a concentration that is peak for their activity. Ethyl alcohol is included for its reduced defatting activity and for activity against viruses, especially the lipophilic group. The inclusion of n-propanol enhances the contribution of alcohol to effectiveness.

A preferred mixture of alcohols is ethanol and n-propanol, each present in an amount of about 40 to about 70% by weight of the composition.

Antimicrobials

Triclosan—This relatively newer type of antimicrobial has a wide spectrum of antimicrobial action, including gram positive and gram negative bacteria. It is also a substantive antimicrobial and is currently incorporated into many cosmetic and drug-type cosmetic products used on the skin. Preferably, the concentrations used are low (in the 0.05 to 0.2 or 0.3% range). However, concentration can be increased to maximize the substantive action and enhance its immediate action.

Chloroxylenol (PCMX or parachlorometaxylenol)—This chemical has been used in products for skin application since 1933. It acts against a broad microbial spectrum, including gram negative organisms and fungi in particular. The concentration utilized in this formula is a preservative-effective amount and is included to inhibit contamination potential when the formulation is applied from multiple-use containers or from reservoirs frequently used in hospital settings.

Emollients—The emollient and humectant ingredients are optionally present to reduce the normal drying and defatting characteristics of alcohol. Preferred emollients are oil of mink and glycerin. Other emollient and/or humectant ingredients include silicone oil and aloe vera.

Surfactants—Surfactants are optionally included as emulsifiers and as a spreading agent in the formula. Preferred surfactants are Dow surfactant and Tween 20.

Perfuming Agents—Optionally, the present invention includes one or more perfuming agents. Preferred perfuming agents are vanilla extract and oil of peppermint. The scent of chloroxylenol is difficult to cover and vanillin is the most often used perfuming agent to cover it. The odor is clean but attractive. This characteristic is important since the majority of users are women.

Chelating Agents—One or more chelating agents are optionally included in the present antimicrobial formulations to enhance their activity against gram negative organisms, Pseudomonas in particular. Disodium edetate is a preferred chelating agent.

The antimicrobial compositions of the present invention can be administered with gimmicks, gadgets, sprays, foams, and attractive formulations that induce personnel to wash their hands. The present formulation can be used in attractive ways such as in a timed spray, an automated machine, a foam application or as a liquid hand rub. A small volume is used and it dries rapidly. A single washing procedure can be executed in 10–15 seconds, or the time routinely given to handwashing, rather than requiring minutes for effectiveness. No aerosols distributing microorganisms and/or microorganisms on skin particles into the air are produced in use. The agitation and friction resulting from the rubbing aids the effectiveness of alcohol. The vigorous rubbing over the hands when the product is used can be adapted to ensure that personnel cover all parts of the hand stressing those parts like the thumbs which are often missed in routine handwashing.

One detracting factor in the analysis of the handwashing practices in hospitals is the lack of convenient sinks for handwashing. An outstanding attribute of alcohol-based products is that no sink or water source is required. This is also an asset in emergency situations.

Another element that is desirable in analyzing the antimicrobial action of products on the skin is persistence, or substantivity of an antimicrobial agent, as dermatologists have termed it.

The definition of substantivity is the binding of a chemical to the dead skin cells of the stratum corneum (top-most layer of the skin). For an antimicrobial, activity is maintained so that bacteria in the hair follicles do not easily re-establish the skin microflora that has been removed. It is uncertain whether there is continued action on bacteria picked up as transient microflora from patient care or procedures, but it is probable that such organisms would not reproduce or establish themselves as resident microflora if this activity is present.

The formula described herein as unique and original combines many of the desirable attributes for a handwashing product for health care and can be applied to other areas where handwashing is becoming important.

The results show that this formula was more effective than a standard isopropanol/quaternary formula and the control, 60 percent isopropyl alcohol, when applied as a timed spray from an automated machine. There was greater than a 4-$\log_{10}$ reduction of organisms artificially applied to the hands.

Minimal inhibitory concentrations of the formula when tested against a panel of organisms showed that the compounds included as active antimicrobials have a broad spectrum of activity.

The hands of personnel involved in the test showed no signs of irritation after the test or as a result of multiple uses in the laboratory.

Tests also showed that microorganisms did not contaminate or colonize the machine when it was operated many times a day (at least 100 time per day).

The present invention is described in greater detail with reference to the following examples, although it is in no way limited thereto.

EXAMPLE 1

A composition was prepared having the following ingredients:

|  | Percent w/v |
|---|---|
| Irgasan DP-300 Triclosan | 1.000 |
| Nipacide PX-PCMX | 0.500 |
| Triton N-101 | 0.010 |
| Disodium Edetate | 0.011 |
| Dow Surfactant 190 | 0.200 |
| Emulan Oil of Mink, light fraction | 0.025 |
| Tween 20 | 0.800 |
| Glycerin, USP | 1.000 |
| Imitation Vanilla Extract | 0.040 |
| Oil of Peppermint, USP | 0.0005 |
| 1-Propanol | 39.550 v/v |
| Alcohol SD40, Anhydrous | 39.550 v/v |
| Distilled Water, qs ad | 100.000 |

Physical Stability

Thirty-five ml were filled into capped 60 ml bottles made of clear glass, high density polyethylene, or high density polypropylene. Duplicate samples were wet down at 56 degrees C., ambient room temperature, and 50 degrees C. Samples were evaluated for changes in weight, color and clarity. Results are tabulated as follows.

| | | Percentage Change in Content Weight | | | |
|---|---|---|---|---|---|
| Condition | Time | Sample | Glass | HDPE | HDPP |
| 5C | 4 mo | A | −0.13 | −0.10 | −0.06 |
| | | B | 0 | −0.03 | −0.10 |
| RT | 10 mo | A | +0.29 | −0.48 | −0.19 |
| | | B | +0.16 | −0.39 | −0.26 |
| 50C | 6 mo | A | +0.06 | −2.18 | −1.20 |
| | | B | +0.19 | −2.26 | −1.56 |

| | | Physical Observations | | |
|---|---|---|---|---|
| Con- | | Container | | |
| dition | Time | Glass | HDPE | HDPP |
| 5C | 4 mo | slight swirl at bottom colorless | white particles present colorless | white particles present colorless |
| RT | 10 mo | clear colorless | clear colorless | clear colorless |
| 50C | 6 mo | clear very slight tan color | hazy very slight tan color | clear very slight tan color |

EXAMPLE 2

Microbiological Testing of a Rapid Acting Formulation for Topical Administration Introduction:

Rapid killing of microorganisms on skin is increasingly an important issue in the nosocomial transmission of infection in medical care facilities. Recent regulations from OSHA and recommendations from CDC have further sharpened the focus on hand washing and gloving in patient care. OSHA has issued regulations concerning the protection of Health Care Workers including requirements for implementation of infection control measures.

Objective:

It was discovered that the combination utilized in the present compositions exhibit unexpected synergism in terms of antimicrobial spectrum and speed of activity. The following studies were designed to show that the complete formulation of the present invention is more effective in rapid killing of high bacterial populations than any of its parts individually.

Materials:

A. Microbial Cultures:
1. *Staphylococcus epidermidis* ATCC 6538
2. *Pseudomonas aeruginosa* 15442
3. *Salmonella choleraesuis* ATCC 10708
4. *Escherichia coli* ATCC 11229
5. *Candida albicans* ATCC 10231
6. *Serratia marcescens* ATCC 14041
7. Group D streptococci Cl 012 (clinical isolate)
8. *Streptococcus faecalis* Cl 154 (clinical isolate)
9. *Staphylococcus epidermidis* ATCC 17917
10. Shigella species Cl 036 (clinical isolate).

B. Microbiological Media:
Trypticase Soy Broth (TSB)
Trypticase Soy Agar (TSA)
Phosphate Buffered Saline (PBS)

C. Miscellaneous Materials
Membrane filters
Filtration equipment
Spectrometer

D. Test Solutions
E. 0.5% chloroxylenol only—in the formulation ID No. 658
F. 1.0% triclosan only—in the formulation ID No. 659
G. 1.0% triclosan complete formulation ID No. 660 0.5% chloroxylenol
H. 40% n-propanol and 40% ethanol
I. 80% ethanol
J. 80% n-propanol Test Procedure:
1. A 24 to 48 hr culture of each organism was standardized spectrophotometrically to provide a culture with a count of $10^9$–$10^{10}$ cfu/ml. The actual count was determined by dilution and plating on TSA.
2. One ml of the adjusted culture was added to 9 ml of PBS.
3. A sterile membrane was wet with 10 ml of PBS.
4. The tube of diluted culture was added to the wetted filter and filtered, leaving the bacteria on the face of the filter.
5. With the filtration was cut off, 3 ml of one of the test solutions was added to the inoculated filter.
6. After a 2-second exposure, diluent was poured onto the filter (at least 25 ml) and filtered immediately.
7. The filter was removed and placed onto the surface of a TSA plate. Incubation was at 35 ±2 degrees C.
8. The number of colonies recovered on the filter was counted after 48-hr incubation.

| | Comparative Results of Formulations Tested | | | | | |
|---|---|---|---|---|---|---|
| | Formulation Code | | | | | |
| Organism Tested | E | F | G | H | I | J |
| 1. *Staphylococcus epidermidis* | TNTC | 0 | 0 | TNTC | TNTC | TNTC |
| 2. *Pseudomonas aeruginosa* | TNTC | TNTC | TNTC | TNTC | TNTC | TNTC |
| 3. *Salmonella choleraesuis* | 3 | 0 | 0 | 6 | 15 | 3 |
| 4. *Escherichia coli* | TNTC | 0 | 0 | TNTC | 250 | 350 |
| 5. *Candida albicans* | TNTC | 300 | 0 | TNTC | 300 | 300 |
| 6. *Serratia marcescens* | TNTC | TNTC | ~400 | TNTC | TNTC | TNTC |
| 7. Group D *streptococci* | 0 | 0 | 0 | 0 | 0 | 0 |
| 8. *Streptococcus faecalis* | 10 | 8 | 0 | ~300 | 31 | 35 |
| 9. *Staphylococcus epidermidis* | 0 | TNTC | 0 | TNTC | TNTC | TNTC |
| 10. *Shigella* species | TNTC | 250 | 0 | TNTC | TNTC | TNTC | note: TNTC = too numerous to count.

The results of this test show that the complete formulation is more effective than any of its mixtures of components. This procedure for testing simulates application of the product to a surface such as skin. The exposure time in the test was extremely short, but in use hospital personnel frequently employ very short exposure times during patient care or in emergency situations.

Conclusions

1. The complete formulation was effective in the test system against a very high challenge counts of a wide variety of microorganisms in a very short period of time.
2. The effectiveness of the complete formulation was more effective than any of the mixtures of the ingredients in the formulation.

What is claimed is:

1. An antimicrobial composition for topical administration comprising from about 0.5 to about 3.0% by weight of triclosan, from about 0.5 to about 2.0% by weight of chloroxylenol, and from about 40 to about 70% by weight of an alcohol or alcohol mixture.
2. An antimicrobial composition according to claim 1, wherein the alcohol is ethanol.
3. An antimicrobial composition according to claim 1, wherein the alcohol is n-propanol.
4. An antimicrobial composition according to claim 1, wherein the alcohol mixture is ethanol and n-propanol.
5. An antimicrobial composition according to claim 1, further comprising an emollient.
6. An antimicrobial composition according to claim 5, further comprising a surfactant.
7. A method for rapidly killing microorganisms on the skin, comprising topical administration to a subject an antimicrobial-effective amount of a composition according to claim 1.

* * * * *